United States Patent [19]

Chakrabarti et al.

[11] Patent Number: 5,380,531
[45] Date of Patent: Jan. 10, 1995

[54] ACCUMULATIONS OF AMINO ACIDS AND PEPTIDES INTO LIPOSOMES

[75] Inventors: Ajoy Chakrabarti; Ian Clark-Lewis; Pieter R. Cullis, all of Vancouver, Canada

[73] Assignee: The Liposome Company, Inc., Princeton, N.J.

[21] Appl. No.: 896,509

[22] Filed: Jun. 2, 1992

Related U.S. Application Data

[63] Continuation of Ser. No. 559,946, Jul. 31, 1990, abandoned.

[51] Int. Cl.⁶ .................................... A61K 9/127
[52] U.S. Cl. .................... 424/450; 264/4.1; 436/829; 428/402.2
[58] Field of Search .............. 424/450; 436/829; 264/4.1; 428/402.2

[56] References Cited

U.S. PATENT DOCUMENTS

| | | | |
|---|---|---|---|
| 3,962,429 | 6/1976 | Furuno et al. | 424/181 |
| 3,993,754 | 11/1976 | Rahman et al. | 424/177 |
| 4,016,100 | 4/1977 | Suzuki et al. | 252/316 |
| 4,145,410 | 3/1979 | Sears | 424/19 |
| 4,193,983 | 3/1980 | Ullman et al. | 424/12 |
| 4,217,344 | 8/1980 | Vanlerberghe et al. | 252/316 |
| 4,224,179 | 9/1980 | Schneider | 252/316 |
| 4,229,360 | 10/1980 | Schneider et al. | 260/403 |
| 4,235,871 | 11/1980 | Papahadjopoulos et al. | 424/14 |
| 4,241,046 | 12/1980 | Papahadjopoulos et al. | 424/19 |
| 4,370,349 | 1/1983 | Evans et al. | 514/785 |
| 4,372,949 | 2/1983 | Kodama et al. | 424/38 |
| 4,389,330 | 6/1983 | Tice et al. | 264/4.1 |
| 4,397,846 | 8/1983 | Weiner et al. | 424/199 |
| 4,411,894 | 10/1983 | Schrank et al. | 424/199 |
| 4,419,348 | 12/1983 | Rahman et al. | 514/34 |
| 4,438,052 | 3/1984 | Weder et al. | |
| 4,460,577 | 7/1984 | Moro et al. | 424/180 |
| 4,485,045 | 11/1984 | Regen | 264/4.3 |
| 4,515,736 | 5/1985 | Deamer et al. | 264/4.3 |
| 4,522,803 | 6/1985 | Lenk et al. | 424/1.1 |
| 4,529,561 | 7/1985 | Hunt et al. | 424/450 |
| 4,532,089 | 7/1985 | MacDonald et al. | 264/4.3 |
| 4,588,578 | 5/1986 | Fountain et al. | 424/1.1 |
| 4,721,612 | 1/1988 | Janoff et al. | 424/1.1 |
| 4,769,250 | 9/1988 | Forssen | 424/450 |
| 4,885,172 | 12/1989 | Bally et al. | 424/417 |
| 4,946,683 | 8/1990 | Forssen | 424/422 |

FOREIGN PATENT DOCUMENTS

| | | | |
|---|---|---|---|
| 2041871 | 9/1980 | United Kingdom . | |
| 2022319B | 2/1982 | United Kingdom | 424/450 |
| 2134869 | 8/1984 | United Kingdom . | |
| 86/00238 | 1/1986 | WIPO . | |
| 86/01102 | 2/1986 | WIPO . | |
| 86/01103 | 2/1986 | WIPO . | |
| 87/02219 | 4/1987 | WIPO . | |
| 88/09168 | 1/1988 | WIPO | 424/450 |
| 88/06442 | 9/1988 | WIPO . | |

OTHER PUBLICATIONS

Bally, et al., "Dopamine Accumlation in Large Unilamellar Vesicles Systems Induced by Transmembrane Ion Gradients", Chem. Phys. Lipids, 47 (1988) 97–107.

(List continued on next page.)

Primary Examiner—Thurman K. Page
Assistant Examiner—G. S. Kishore
Attorney, Agent, or Firm—Allen Bloom; Kenneth B. Rubin

[57] ABSTRACT

The present invention relates to liposomal compositions having a concentration gradient which load amino acids and peptides exhibiting weak acid or base characteristics into liposomes. Specifically loaded into liposomes by the methods of the present invention are C-terminal substituted amino acids or peptides. The liposomes are preferably large unilamellar vesicles. The concentration gradient is formed by encapsulating a first medium in the liposomes, said medium having a first concentration of the one or more charged species, and suspending the liposomes in a second medium having a second concentration of the one or more charged species, such as for example a pH gradient. Also disclosed are pharmaceutical preparations comprising such C-terminal substituted amino acids or peptides which have been loaded into the liposomes by the method of the invention.

16 Claims, 3 Drawing Sheets

OTHER PUBLICATIONS de Kroon et al., "Association of Synthetic Model Peptides with Phospholipid Vesicles Induced by a Membrane Potential", BBA, 981 (1989) 371–373.

Fiske, et al., "The Colorimetric Determination of Phosphorus", *J. Biol. Chem.* 66:375–379 (1925).

Hope, et al., 1987 Biochim. Biophys. Acta., 812.55, "Production of Large Unilamellar Vesciles by a Rapid Extrusion Procedure. Characterization of Size Distribution, Trapped Volume and Ability to Maintain a Memebrane Potention".

Hope, et al., "Lipid Asymmetry Induced by Transmembrance pH Gradients in Large Unilamellar Vesicles", J. Biol. Chem. 262 (1987), 9, 4360–4366.

Koppel, "Analysis of Macromolecular Polydispersity in Intesity Correlation Spectroscopy: The method of Cumulants", J. Chem. Phys. 57 (1972), 11, 4814–4820.

Madden, et al., "The Accumalation of Drugs within Large Unilamellar Vescisles Exhibiting a Proton Gradient: A Survey", Chem. Phys. Lipids, 53, (1990) 37–46.

Mayer, et al., "Uptake of Adriamycin into Large Unilamellar Vesicles in Response to a pH Gradient", BBA, 857 (1986) 123–126.

Mayer, et al., "Influence of Ion Gradients on the Transbilayer Distribution of Dibucaine in Large Unilamellar Vesicles", Biochemistry, 27, (1988), 2053–2060.

Mayer, et al., "Techniques for Encapsulating Bioactive Agents into Liposomes", Chem. Phys. Lipids, 40 (1986) 333–345.

Abra, et al., 1983, Cancer Chemother. Pharmacol, 11:98, "Delivery of Therapeutic Doses of Doxorubicin in the Mouse Lung Using Lung–Accumulating Liposomes Proves Unsuccessful".

Akerman, et al., 1976, Biochim. Biophys. Acta., 426:624, "Stacking of Safranine in Liposomes During Valinomycin Induced Efflux of Potassium Ions".

Bally, et al., 1985, Biochim. Biophys. Acta., 812:66, "Uptake of Saframine and Other Lipophilic Cations into Model Membrane System in Response to a Membrane Potential".

Bottcher, et al. 1961 Anal. Chim. Acta., 24:203–204, "A Rapid and Sensitive Sub–Micro Phosphorus Determination".

Burke et al., Chem. Abstracts, vol. 102, No. 3, Jan. 21, 1985.

Cafisco, et al., 1983, Biophys. J. 44:49, "Electrogenic H+/OH− Movement Accorss Phospholipid Vesicles Measured by Spin–Labeled Hydrophobic Ions".

Casey et al., "Active Proton Uptake by Chromaffin Granules: Observation by Amine Distribution and Phosphorous—31 Nuclear Magnetic Resonance Techniques", 1977 Biochemistry 16(5) pp. 972–976.

Chemical Abstracts 103:174355e.

Chemical Abstracts 99:49240m.

Chen, et al., 1956, Analytical Chem., 11:1756–1758, "Microdeterination of Phosphorus".

Corda, et al., J. Membr. Bio., 1982 65(3) 235–42, "Increase in Lipid Microviscosity of Unilamellar Vesicles upon the Creation of Transmembrane Potential", Chem. Abs. vol. 96, 1982, Abs. 176569p.

Cramer and Prestegard, "NMR Studies of pH–Induced Transport of Carboxylic Acids Across Phospholipid Vesicle Membranes", Biochem. Res. Commun. 1977, 75(2) pp. 295–301.

Crommelin, et al. "Preparation and Characterization of Doxorubicin–containing liposomes II. Capacity. Long Term Stability and Doxorubicin–bilayer interaction mechanism", Abst. 109032w., Int. J. Pharm. 1983, 17(2–3) 135–44.

Crommelin, et al., 1983, Int. J. Pharm. 16(1):79 "Preparation and Characterization of Doxorubicin–Containing Liposomes: I. Influence of Liposome Charge and pH of Hydration Medium on Loading Capacity and Particle Size".

Crommelin, et al., "Stability of Liposomes on Storage: Freeze Dried, Frozen or as an Aqueous Dispersions", Phar. Res. (1984) pp. 159–163.

Cullis, et al., "Generating and loading of liposomal systems for drug–delivery applications", Adv. Drug, Delivery, Rev, 3, (1989) 267–282.

Deamer, 1983, in: Liposomes, 1983, M. Ostro (ed.), Marcel Dekker, New York.

Deamer, et al., "The Response of Fluorescent Amines to pH Gradients Across Liposomes Membranes", 1972, Biochemi. Biophys. Acta, 274, pp. 323–335.

(List continued on next page.)

OTHER PUBLICATIONS

Forssen, et al., 1983, Cancer Res., 43:546, "Improved Therapeutic Benefits of Doxorubicin by Entrapment in Anionic Liposomes".

Gabizon, et al., 1982, Cancer Res. 42-4734, "Liposomes as in Vivo Carriers of Adriamycin:Reduced Cardiac Uptake and Preserved Antitumor Activity in Mice".

Garcia, et al., 1983, Biochemisty 22(10):2524, "Mechanism of Lactose Translocation in Proteoliposomes Reconstituted with Iac Carrier Protein Purified from *Escherichia coli*. 1. Effect of pH and Imposed Membrane Potential on Efflux, Exchange, and Counterflow".

Gierasch, L., "Signal Sequences", Biochemistry, 28(3), Feb. 1989, 923–930.

Gutknecht, et al. "Histamine, Theophylline and Tryptamine Transport Through Lipid Bilayer Membranes", BBA, 649, (1981), 149–154.

Herbette, et al., Chem. Abstracts, vol. 102, No. 3, Jan. 21, 1985.

Hope, et al., "Phospholipid Asymmetry in Large Unilamellar Vesciles Induced by Transmembrane pH Gradient", Biochemistry, 1989, 28, 4181.

Jonah, et al., 1975, Biochim, et Biophys. Acta 401:336-348, "Tissue Distribution of EDTA Encapsulated Within Liposomes of Varying Surface Properties".

Kano, et al., 1977, Life Sciences, 20:1729, "Enhanced Uptake of Drugs in Liposomes" Use of Lavile Vitamin B12 Complexes of 6-Mercaptopurine and 8-Azaguanine.

Kano and Fendler, "Pyranine as a Sensitive pH Probe for Liposome Interiors and Surfaces", Biochemic. Biophys Acta. 1978, 509, pp. 289–299.

Kirby and Gregoriadis, "The Effect of Lipid Composition of Small Unilamellar Liposomes Containing Melphalan and Vincristine on Drug Clearance After Injection into Mice", Abstract of Biochem. Pharmacol. 1983, 32(4) pp. 609–615.

Kirby, et al., 1984 in *Liposome Technology*, vol. 1, Preparation of Liposomes, G. Gregoriadias, et. pp. 19–27, "A Simple Procedure for Preparing Liposomes Capable of High Encapsultion Efficiency Under Mild Conditions".

Kirby, et al., 1984, Bio/Technology, 2(11):979, "Dehydration-Rehydraton Vesicles: A Simple Method for High Yield Drug Entrapment in Liposomes".

Kornberg, et al., "Measurement of Transmembrane Potentials in Phospholipid Vesicles", 1972, Proc. Nat. Aca. Sci. USA 69(6), pp. 1508–1513.

Lenk, et al., "Stabilized Purilamellar Vesicles: A New Type of Liposome", Abstract No. 83980x.

Lenk, et al. "Stable plurilamellar vesicles", Chemical Abstracts, vol. 100, 1984, 215560b.

Mauk, et al., 1979, PNAS, USE 76:765, "Preparation of Lipid Vesicles Containing High Levels of Entrapped Radioactive Cations".

Mayhew et al., Biol Cell (1981) 1983 47(1) 81–5, Chem. Abs. vol. 98, 1983, Abs. 221734t.

Mayer, et al., "Uptake of Dibucaine into Large Unilamellar Vesicles in Response to a Membrane Potential", J. Biol. Chem, 260, 2, 1985, 802–808.

Mayer, et al., "Uptake of anitneophastic agents into Large Unilamellar Vesicles in Response to a Membrane Potential", BBA, 816 (1985), 294–302.

Mayer, et al., "Solute Distribution and trapping efficiencies observed in freeze-thawed multilamellar vesicles", BBA, 817 (1985), 193–196.

Mayer, et al., "Influence of Ion Gradients on the Transbilayer Distribution of Dibucaine in Large Unilamellar Vesicles", Biochemistry 27, (1988), 2053–2060.

McLaughlin et al, J. Gen. Physiol. 1981, 77(4) 445–73, Chemical Abs. vol. 94, 1981, Abstract 169846g.

Morii, et al., 1983, Int. J. Pharm. 17(2–3), 215–224, "Size and Permeability of Liposomes Extruded Through Polycarbonate Membranes".

Moro, et al., "Purification of Liposome Suspension", Chem. Abstract, vol. 94, 1981, 52931a.

Nichols, et al., 1976, Biochim. Biophys. Acta., 455:269, "Catecholamine Uptake and Concentration by Liposomes Maining pH Gradients".

Olson, Eur. J. Cancer Clin. Oncol., 18:167, "Character- (List continued on next page.)

OTHER PUBLICATIONS ization, Toxicity and Therapeutic Efficacy of Adriamycin Encapsulated in Liposomes".

Olsnes, et al., "Diphtheria Toxin entry: Protein Translocation in the Reverse Direction", Trends in Biochem, Sci., 13 (1988), 348.

Papahadjopoulos, et al, 1980, in Liposomes and Immunology, 1980, Tom and Six, eds., Elsevier, New York, "Optimization of Liposomes as a Carrier System for the Intracellular Delivery of Drugs and Macromolecules".

Pick, 1981, Arch. Biochem. Biophuys., 212(1), 186–194, "Liposomes with a Large Trapping Capacity Prepared by Freezing and Thawing of Sonicated Phospholipid Mixtures".

Rahman, et al., 1982 Cancer Res. 42:1817, "Doxorubicin–Induced Chronic Cardiotoxicity and Its Protection by Lipsomal Administration".

Redelmeier, "On the mechanism of transbilayer Transport of Phosphatidylglycerol in Response to Transmembrane pH Gradients", Biochemistry, 29, (1990), 3046–3053.

Rosa, et al., 1982, in: Transport in Biomembranes, 1982, R. Antolini et al., (ed), Raven Press, New York, "Liposomes Containing Doxorubicin: An Example of Drug Targeting".

Rosa, et al., 1983 Pharmacol., 26:221, "Absorption and Tissue Distribution of Doxorubicin Entrapped in Liposomes Following Intraveous or Intraperitoneal Administration".

Shakhov, et al., 1984, Biokhimika, 48(8):1347, "Reconsitution of Highly Purified Proton–Translocating Pyrothosphatas".

Singleton, et al., 1965, J. Am. Oil Chem. Soc. 42:53–56, "Chromatographically Homogeneous Lecithin from Egg Phospholipids".

Szoka, et al., "Comparative Properties and Method of Preparation ofLipid Vesicles (Liposomes), Ann. Rev. Biophys. Bioeng. 1980, 9:467–508.

van Hoesel, et al., 1984, Cancer Res., 44:3698, "Reduced Cardiotoxicity and Nephrotoxicity with Preservation of Antitumor Activity of Doxorubicin Entrapped in Stable Liposomes in the LOU/MN Wsi Rat".

Verner, et al, "Protein Translocation Across Membranes", Science, 241 (1988), 1307.

ACCUMULATIONS OF AMINO ACIDS AND PEPTIDES INTO LIPOSOMES

This is a continuation of copending application Ser. No. 559,946 filed on Jul. 31, 1990, now abandoned.

Several biogenic amines and antineoplastic agents have been shown to accumulate in liposomes in response to an imposed proton gradient known as "remote loading" [See, for example Mayer, et al., Biochim. Biophys. Acta, 857, 123, (1986), Mayer, et al., Biochemistry, 27, 2053, (1988) and M. B. Bally, et al., Chem. Phys. Lipids, 47, 97, (1988)]. This loading technique allows independent variation of any of the liposomal parameters. Much higher drug to lipid ratios can be achieved in comparison to conventional techniques [Mayer, et al. Chem. Phys. Lipids, 40, 333 (1986)]. In addition, the transmembrane distribution of the drug is generally determined by the proton gradient which modulates drug leakage by changes in the buffering capacity of the intravesicular medium.

The use of proton and other ion gradients to trap drugs which are non-zwitterionic weak bases has been shown to be practical for adriamycin, the local anaesthetics dibucaine and dopamine and other drugs. Advantages of this system include efficient drug trapping, slower rates of drug release than passively trapped drug, and higher drug to lipid ratios than can otherwise be achieved.

In addition, because the liposomes can be prepared in the absence of the drug, problems with drug release during storage, or drug degradation during liposomal preparation can be avoided. Intraliposomal drug accumulation in response to pH gradients is believed to occur in a manner similar to that of other weak bases, for example, the pH gradient probe methylamine. Methylamine equilibrates across liposomal membranes in the uncharged form, and reionizes according to the Henderson-Hasselbach relationship of the pH of its environment. The equilibrium distribution reflects the transmembrane pH gradient, and its redistribution can be used to measure these gradients. However, not all agents which possess the capacity to be ionized according to Henderson-Hasselbach relationships accumulate in liposomes according to this relationship. In fact, certain agents do not seem to accumulate at all. In addition, certain agents which may accumulate according to this relationship immediately undergo release, resulting in unworkable formulations which must be used immediately after production and which are virtually unusable as sustained release products.

Liposomes are completely closed lipid bilayer membranes which contain entrapped aqueous volume. Liposomes are vesicles which may be unilamellar (single membrane) or multilamellar (onion-like structures characterized by multiple membrane bilayers, each separated from the next by an aqueous layer). The bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase.

It is an aspect of the present invention to disclose the loading of certain amino acids and peptides which exhibit weak acid or base characteristics. The amino acids and peptides of this aspect of the invention are more specifically those wherein the C terminal and other carboxyl functions have been modified by substitution thereof, and associated with a functional group such as for example an ester or an amide. More specifically, basic amino acids and peptides of the invention have been modified to methyl ester, ethyl ester or amide forms.

The loading via a transmembrane concentration gradient, more specifically, a transmembrane pH gradient, occurs for certain amino acids and peptides wherein the C-terminal carboxyl function is substituted, wherein the amino acid or peptide would exhibit weak acid or base characteristics, and more specifically, wherein such amino acid or peptide carboxyl function is modified to a non-acidic group such as an amide or a methyl ester. Such amino acid and peptide derivatives exhibit weak base characteristics. Such amino acids and peptides load into LUVs by methods of the invention in response to a transmembrane concentration gradient (for example a transmembrane pH gradient) (inside acidic).

The methods of the invention result in transmembrane concentration gradient-driven loading for the amino acid derivatives lysine methyl ester, lysine amide, lysine ethyl ester, and the peptides Bombesin (pGlu-Gln-Arg-Leu-Gly-Asn-Gln-Trp-Ala-Val-Gly-His-Leu-Met-$NH_2$), Gastrin-Related Peptide (N-t-BOC-Trp-Met-Asp-Phe-Amide), and Growth Hormone Releasing Factor Fragment (Lys-Tyr-Trp-Trp-Phe-$NH_2$).

The methods of the invention, however, do not result in loading into LUVs of certain other amino acids and peptides, for example, the peptides Histidine methyl ester, $(Lys)_5$ methyl ester and $(Lys-(Ala)_4)$ methyl ester cannot be loaded into liposomes by the methods of the invention.

SUMMARY OF THE INVENTION

Figure 1:
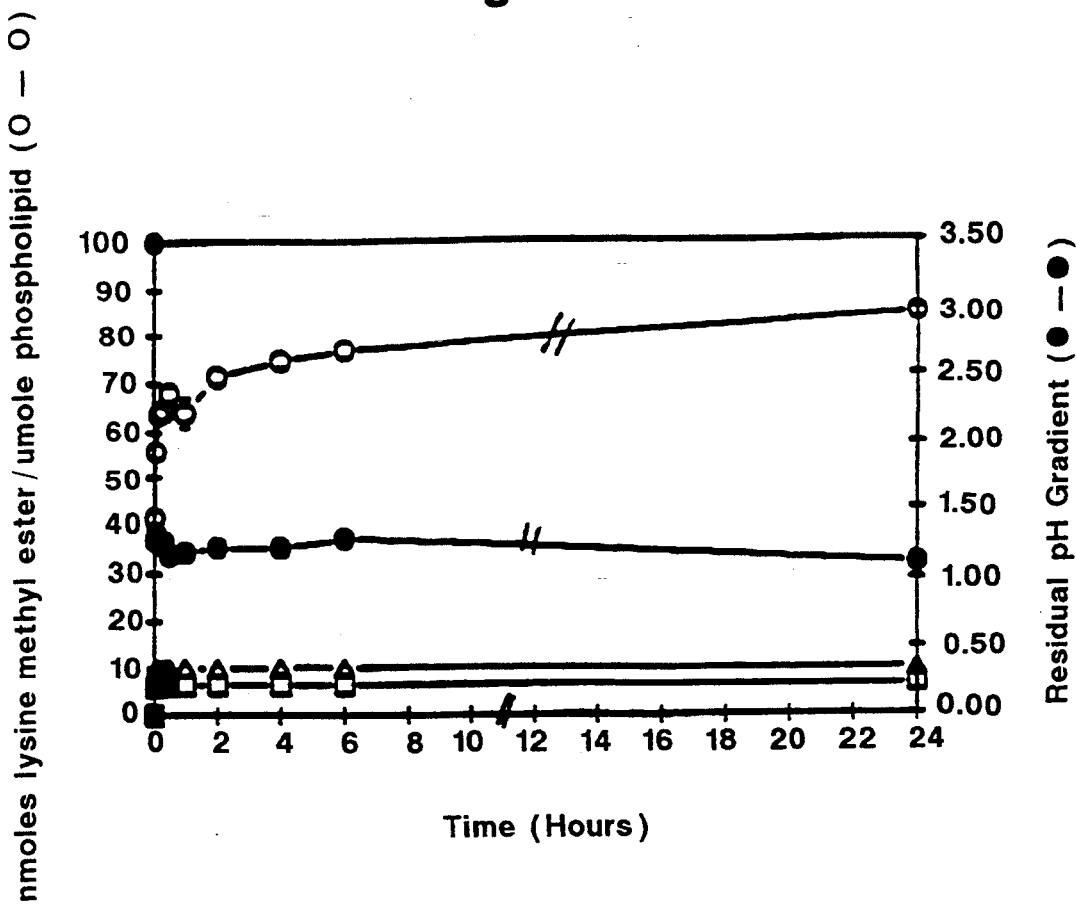
FIG. 1 graphically represents the time course of lysine methyl ester into 100 nm EPC vesicles bearing a 7.5/4.0 (external/internal) pH gradient (open circles). Control vesicles with no pH gradient (7.5/7.5—open triangles) and 4.0/4.0—open squares) were also tested. Uptake was conducted at 20° C. The external concentration of lysine methyl ester was 1.3mM.

The present invention relates to liposomal compositions having a pH gradient, such liposomes exhibiting markedly increased accumulation of amino acids and peptides as expected from the Henderson-Hasselbach relationship, by formulating the liposomes utilizing a first internal aqueous buffer and a second external aqueous buffer, the first and second buffers differing as to ionic (proton) concentration.

The present invention is further directed to a method for loading liposomes with a C-terminal carboxyl function substituted amino acid or peptide, therefore wherein the amino acid or peptide would exhibit weak acid or base characteristics, and more specifically, wherein such amino acid or peptide carboxyl function is modified to a non-acidic group such as an amide or a methyl ester. Such amino acid and peptide derivatives exhibit weak base characteristics.

The loading includes preparing liposomes having a concentration gradient of one or more charged species across their membranes, said concentration gradient being capable of generating a transmembrane potential having an orientation which will cause the peptide to be loaded into the liposomes, and admixing the amino acid or peptide with the liposomes. The liposomes are those that can be formed by any method but are preferably large unilamellar vesicles. The concentration gradient is formed by encapsulating a first medium in the liposomes, said medium having a first concentration of the one or more charged species, and suspending the liposomes in a second medium having a second concentration of the one or more charged species. Such a concentration gradient can be for example, a pH gradient.

The amino acid and peptide derivatives which can be loaded by the transmembrane concentration gradient method of the invention include the amino acid derivatives lysine methyl ester, lysine amide, lysine ethyl ester, and the peptides Bombesin (pGlu-Gln-Arg-Leu-Gly-Asn-Gln-Trp-Ala-Val-Gly-His-Leu-Met-NH$_2$), Gastrin-Related Peptide (N-t-BOC-Trp-Met-Asp-Phe-Amide), Growth Hormone Releasing Peptides Tyr-Gly-Trp-Phe-Phe-Amide and Trp-Ala-Trp-Phe-Ala-Amide, and Growth Hormone Releasing Factor Fragment (Lys-Tyr-Trp-Trp-Phe-NH$_2$).

The peptides Histidine methyl ester, Trp-Nle-Arg-Phe-Amide (molluscan cardioexcitatory neuropeptide analog), p-Glu-Ser-Leu-Arg-Trp-Amide (sea anemone neuropeptide), Lutenizing Hormone Releasing Hormone (pGlu-His-Trp-Ser-Tyr-Gly-Leu-Arg-Pro-Gly-NH$_2$), Lys$^8$-Vasopressin (Cys-Tyr-Phe-Gln-Asn-Cys-Pro-Lys-Gly-NH$_2$),(Lys)$_5$ methyl ester and (Lys-(Ala)$_4$) methyl ester cannot be loaded into liposomes by the methods of the invention.

Also disclosed are pharmaceutical preparations comprising such C-terminal substituted amino acids or peptides which have been loaded into the liposomes by the method of the invention.

The loading method proceeds by admixing the amino acid or peptide derivative with liposomes having a transmembrane potential across their membranes, the orientation of the transmembrane potential being such that if the agent is positively charged, the internal potential of the liposomes is negative to the potential of the external medium, and if the agent is negatively charged, the internal potential of the liposomes is positive relative to the potential of the external medium. The transmembrane potential can be produced by creating a concentration gradient of one or more charged species across the liposomes membranes, such as for example H$^+$ ions, wherein the concentration gradient is a pH gradient.

In general, the liposome compositions of the present invention may comprise phospholipids such as egg phosphatidylcholine (EPC), hydrogenated soy phosphatidylcholine, distearoylphosphatidylcholine, dimyristoylphosphatidylcholine, or diarachidonylphosphatidylcholine, among others, and may additionally comprise a number of steroidal compositions, as well as other compositions.

When the liposomal compositions additionally comprise steroidal compositions, these may include cholesterol, which may be used preferably in a 55:45 (lipid:steroidal lipid) mole ratio.

DETAILED DESCRIPTION OF THE INVENTION

The present invention discloses efficient trapping of amino acids and peptides in liposomes exhibiting a transmembrane ionic gradient, preferably a transmembrane pH gradient.

The amino acid and peptide derivatives which can be loaded by the transmembrane concentration gradient method of the invention include the amino acid derivatives lysine methyl ester, lysine amide, lysine ethyl ester, and the peptides Bombesin (pGlu-Gln-Arg-Leu-Gly-Asn-Gln-Trp-Ala-Val-Gly-His-Leu-Met-NH$_2$), Gastrin-Related Peptide (N-t-BOC-Trp-Met-Asp-Phe-Amide), and Growth Hormone Releasing Factor Fragment (Lys-Tyr-Trp-Trp-Phe-NH$_2$).

The peptides Histidine methyl ester, (Lys)$_5$ methyl ester and (Lys-(Ala)$_4$) methyl ester cannot be loaded into liposomes by the methods of the invention.

The liposomes of the present invention may be formed by any of the methods known in the art, but preferably they are formed according to the procedures disclosed in Bally et al., copending U.S. application Ser. No. 07/284,751, filed Dec. 12, 1988, U.S. Pat. No. 5,077,056 and Mayer et al. copending U.S. application Ser. No. 07/636,015, filed Jan. 4, 1991. These techniques allow the loading of liposomes with ionizable agents to achieve interior concentrations considerably greater than otherwise expected from the agents' solubility in aqueous solution at neutral pH and/or concentrations greater than can be obtained by passive entrapment techniques.

In this technique, a transmembrane ion (pH) gradient is created between the internal and external membranes of the liposomes and the agent is loaded into the liposomes by means of the ion (pH) gradient, which drives the uptake. The transmembrane gradient is generated by creating a concentration gradient for one or more charged species, for example Na+, Cl−, K+, Li+, OH− and preferably H+, across the liposome membranes, such that the ion gradient drives the uptake of ionizable agents across the membranes.

In the present invention, transmembrane ion (H+) gradients are preferably employed to produce the ion gradient and load the agents, which tend to have weakly basic nitrogen groups, into the liposomes. In the present invention, liposomes are preferably first formed in an aqueous buffer solution. The first solution is either acidic or basic, depending upon whether the agent to be loaded produces a charged species at basic or acidic pH. For example, in the case of loading weakly basic agents, a charged species is produced at low pH, i.e., a pH of about 2.0 to 5.0, preferably a pH of about 4.0. After formation of liposomes having an acidic internal aqueous buffer solution, the buffer solution external to the liposomes is then modified to a pH significantly above the pH of the internal buffer solution, preferably at least about 3.0 to 4.0 pH units above the internal buffer solution.

The modification of the external buffer results in a pH gradient which drives the accumulation of the agent within the liposome. In general, the agent will pass through the lipid layer(s) of the liposome in its uncharged form much more readily than it will in its charged (protonated, in the case of weakly basic agents) form. Thus, uncharged agent in the external buffer will readily pass through the liposome into the internal buffer, become protonated, and remain within the liposome as a "trapped" protonated molecule which does not readily pass through the liposome layer(s). Agent will thus concentrate in the liposome as a function of the pH gradient between the internal and external buffer solutions.

For a typical liposome preparation technique as fully described hereinbelow, the first aqueous buffer solution will surround the liposomes as they are formed, resulting in the buffer solution being internal and external to the liposomes. To create the concentration gradient, the original external buffer solution may be acidified or alkalinized so that the concentration of charged species differs from the internal buffer, or alternatively, the external buffer may be replaced by a new external medium having different charge species. The replacement of the external medium can be accomplished by various techniques, such as by passing the liposome preparation through a gel filtration column, e.g., a Sephadex column, which has been equilibrated with the new medium, or by dialysis or related techniques.

In the present invention, liposome compositions are preferred which are formed utilizing a first internal buffer solution of acidic character (pH about 3.0 to 5.0) and a second external buffer solution, the pH of which is preferably between about 6.5 and 8.0, preferably 7.5. The low pH of the internal buffer relative to a more basic or neutral pH of the external buffer produces a transmembrane gradient which acts to drive the accumulation of the agent in the liposome.

Lipids which can be used in the liposome formulations of the present invention include synthetic or natural phospholipids and may include phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM) and cardiolipin, among others, either alone or in combination. The phospholipids useful in the present invention may also include dimyristoylphosphatidylcholine (DMPC) and dimyristoylphosphatidylglycerol (DMPG). In other embodiments, distearoylphosphatidylcholine (DSPC), dipalmitoylphosphatidylcholine (DPPC), or hydrogenated soy phosphatidylcholine (HSPC) may also be used. Dimyristoylphosphatidylcholine (DMPC) and diarachidonoylphosphatidylcholine (DAPC) may similarly be used.

Due to the elevated transition temperatures ($T_c$) of lipids such as DSPC ($T_c$ of about 65° C.), DPPC ($T_c$ of about 45° C.) and DAPC ($T_c$ of about 85° C.), such lipids are preferably heated to about their $T_c$ or temperatures slightly higher, e.g., up to about 5° C. higher than the $T_c$ in order to make these liposomes.

In preferred embodiments, egg phosphatidylcholine is used. In a number of embodiments of the present invention, a steroidal component may be added to the liposome, regardless of the phospholipid chosen. Such a steroidal component may for example be selected from the group consisting of cholesterol, cholestanol, coprostanol or cholestane. In addition, polyethylene glycol derivatives of cholesterol (PEG-cholesterols), as well as organic acid derivatives of sterols, for example cholesterol hemisuccinate (CHS) may also be used in combination with any of the above-mentioned phospholipids. Organic acid derivatives of alpha-tocopherol hemisuccinate, (THS) may also be used. CHS- and THS-containing liposomes and their tris salt forms may generally be prepared by any method known in the art for preparing liposomes containing sterols.

Any of the above-mentioned sterols may be used in liposomes, so long as the resultant phospholipid-sterol mixture yields stable liposomes. In particular, see the procedures of Janoff, et al., U.S. Pat. No. 4,721,612, issued Jan. 26, 1988, entitled "Steroidal Liposomes", and Janoff, et al., U.S. Pat. No. 4,861,580, issued Aug. 29, 1989, relevant portions of which are incorporated by reference herein. In certain embodiments in which the liposomes are designed to prevent rapid release of the agent, cholesterol in an amount equal to about 30 mole % to about 45 mole % by weight of the lipid comprising the liposome is preferably used in combination with any of the above-named phospholipids or phospholipid/steroid combinations. Such compositions should, in general, prevent the undesired rapid release of accumulated agent from the liposome. Any combination of membrane-stabilizing component and lipid may be used which prevents rapid release of agents from the liposome, and one of ordinary skill in the art will be able to modify the membrane-stabilizing component and the phospholipid to formulate liposomes which prevent rapid release of the agent.

Most preferably, liposomes comprising either phosphatidylcholine or a mixture of about 45 mole % by weight cholesterol and about 55 mole % by weight phosphatidylcholine are used in this aspect of the present invention.

Several methods may be used to form the liposomes of the present invention. For example, multilamellar vesicles (MLVs), stable plurilamellar vesicles (SPLVs), or reverse phase evaporation vesicles (REVs) may be used. Preferably, however, MLVs are extruded through filters forming large unilamellar vesicles (LUVs) of sizes dependent upon the filter size utilized. In general, polycarbonate filters of 30, 50, 60, 100, 200 or 800 nm pores may be used. In this method, disclosed in Cullis, et al., U.S. Pat. No. 5,008,050, issued Apr. 16, 1991, relevant portions of which are incorporated by reference herein, the liposome suspension may be repeatedly passed through the extrusion device resulting in a population of liposomes of homogeneous size distribution.

For example, the filtering may be performed through a straight-through membrane filter (a Nuclepore polycarbonate filter) or a tortuous path filter (e.g. a Nuclepore Membrafil filter (mixed cellulose esters) of 0.1 μm size), or by alternative size reduction techniques such as homogenization. The size of the liposomes may vary from about 0.03 to above about 2 microns in diameter; preferably about 0.05 to 0.3 microns and most preferably about 0.1 to about 0.2 microns. The size range includes liposomes that are MLVs, SPLVs, or LUVs.

In the present invention, the preferred liposomes are those which are unilamellar liposomes of about 0.1 to about 0.2 microns. As described hereinabove, a number of lipids may be used to form liposomes having a gel to liquid crystalline Tc above ambient temperature. In such cases, an extruder having a heating barrel or thermojacket may be employed. Such a device serves to increase the liposome suspension temperature allowing extrusion of the LUVs. The lipids which are used with the thermojacketed extruder are, for example, DSPC, DPPC, DMPC and DAPC or mixtures thereof, which may include cholesterol in certain embodiments for preventing the rapid release of agents from the liposome. Liposomes containing DSPC are generally extruded at about 65° C., DPPC at about 45° C. and DAPC at about 85° C. (about 5° C. above the lipid $T_c$).

As indicated, the preferred liposome for use in the present invention are LUVs of about 0.06 to about 0.3 microns in size. As defined in the present application, a homogeneous population of vesicles is one comprising substantially the same size liposomes, and may have a Gaussian distribution of particle sizes. Such a population is said to be of uniform size distribution, and may be unimodal with respect to size. The term "unimodal" refers to a population having a narrow polydispersity of particle sizes, and the particles are of a single "mode". A liposomal population is unimodal if, when measured by quasi elastic light scattering methods, the population approximates to a Gaussian distribution, and if a second order polynomial will fit the natural logarithm of the autocorrelation function of a sample (Koppel, 1972, J. Chem. Phys., 57:4814). The closer this fit, the better the measure of unimodality. The closeness of this fit may be determined by how close the chi square ($chi^2$) value of the sample is to unity. A $chi^2$ value of 2.0 or less is indicative of a unimodal population.

Other size reduction techniques may be employed in practicing the present invention. For example, homogenization or milling techniques may successfully be employed. Such techniques may yield liposomes that are homogeneous or unimodal with regard to size distribution. Liposomes may be prepared which encapsulate the first aqueous buffer solution having the characteristics described hereinabove.

During preparation of the liposomes, organic solvents may also be used to suspend the lipids. Suitable organic solvents for use in the present invention include those with a variety of polarities and dielectric properties, which solubilize the lipids, for example, chloroform, methanol, ethanol, dimethylsulfoxide (DMSO), methylene chloride, and solvent mixtures such as benzene:methanol (70:30), among others. As a result, solutions (mixtures in which the lipids and other components are uniformly distributed throughout) containing the lipids are formed. Solvents are generally chosen on the basis of their biocompatability, low toxicity, and solubilization abilities.

One preferred embodiment of the present invention is a 3 component liposomal-agent treatment system which allows for highly efficient entrapment of the agent at the clinical site. When the agent is one that loads in response to a transmembrane pH gradient where the interior of the liposome is acid, the first component of the system (Vial 1) comprises liposomes in an acidic aqueous or buffer solution, for example, citric acid buffer (at about 300 mM, pH about 3.8 to 4.2, preferably 4.0).

The second component of the system (Vial 2) comprises a relatively basic buffer or aqueous solution, for example, a sodium carbonate or sodium bisphosphate solution, or a sodium chloride/HEPES buffered saline solution ("HBS") at pH about 10 to 12, preferably about pH 11.5, which serves to become part of the external aqueous or buffer solution of the liposome formulation.

The third component (Vial 3) is the agent to be entrapped. The above-described treatment system may be provided as a 3-vial system, the first vial containing the liposomes in acidic medium, the second vial containing the solution of relative alkalinity, and the third vial containing the amino acid or peptide derivative (the agent), as described hereinabove. A similar treatment system may be provided for an agent that loads in response to a transmembrane gradient wherein the internal buffer of the liposomes is relatively basic i.e., has a pH about 8.5-11.5. In such a case, the first vial would contain the liposomes in relatively alkaline medium, the second vial would contain the solution of relative acidity, and the third vial, the agent to be entrapped.

Following the formation of the pH gradient across the liposomes (by admixing the first and second vials), the liposomes may be heated prior to admixing with the amino acid or peptide. Under certain circumstances, and in cases where the agent is to be loaded into liposomes comprising at least about 30 mole % cholesterol to minimize the rapid release of the agent, it may be advantageous to heat the liposomes to facilitate loading, up to some temperature appropriate to the liposome composition and the presence of the amino acid or peptide. Loading, for example, may take place at temperatures of from about 4° C. to about 60° C.

To load the agent(s) into the liposomes utilizing the above-described treatment systems, the methods described in Mayer, et al. copending U.S. application Ser. No. 07/636,015, filed Jan. 4, 1991, relevant portions of which are incorporated by reference, herein may be modified for use with the agents of the present invention.

In a liposome-agent delivery system, the agent is entrapped in or associated with the liposome and then administered to the patient to be treated. For examples wherein the agents are drugs, see Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,114,179; Lenk et al., U.S. Pat. No. 4,522,803; and Fountain et al., U.S. Pat. No. 4,588,578. As used throughout the specification, the terms amino acid and peptide, and the term agent, are used interchangeably.

The choice of buffer to use as the internal buffer solution may vary depending upon the agent chosen for loading. One of ordinary skill in the art will be able to assess the relative solubilities of ionized species of a particular agent and the buffer strength to determine the buffer solution to be used as the internal buffer solution. Any buffer solution having the characteristics generally described hereinabove may be used in the present invention, provided that the solution is pharmaceutically compatible, when necessary, i.e., wherein the solution may be administered to the patient without deleterious affects.

Typical internal buffer solutions include citric acid, oxalic acid, succinic acid and other organic acid salts being preferred, among others. Citric acid in a concentration ranging from about 100 mM to about 300 mM is preferred. Most preferably, the citric acid buffer solution has a concentration of about 300 mM.

Typical external buffer solutions may include NaCl, KCl, potassium phosphate, sodium bicarbonate, sodium carbonate, sodium bisphosphate, potassium sulfate, (N-2-Hydroxyethyl Piperazine-N'-2-Ethane Sulfonic Acid) or "HEPES", 2-[N-morpholino] ethane-sulfonic acid or "MES", N-(2-Hydroxyethyl)piperazine-N'-3-propane-sulfonic acid or "EPPS", 2-[N-Cyclohexylamino] ethane-sulfonic acid or "CHES", Piperazine-N,N'-bis [2-ethane-sulfonic acid] or "PIPES", and mixtures thereof, among others. In the present invention, the preferred external buffer solution is NaCl/HEPES, and more preferably 150 mM $Na_2SO_4$, 20 mM HEPES at pH 7.5.

Loading efficiencies of agents utilizing the present invention generally range from about 20% up to about 100%, preferably at least about 50%. In general, the loading efficiencies for agents according to the present invention are as expected from the Henderson-Hasselbach relationship. Of course, not all agents readily accumulate in liposomes according to the Henderson-Hasselbach relationship, and certain agents (see Comparative Examples 13, 14 and 15) appear, in certain cases, not to accumulate at all.

The liposomes formed by the procedures of the present invention may be lyophilized or dehydrated at various stages of formation. For example, the lipid film may be lyophilized after removing the solvent and prior to adding the agent or forming the liposomes through hydration of the film. Such dehydration may be carried out by exposure of the lipid or liposome to reduced pressure thereby removing all suspending solvent.

The liposomes themselves may be dehydrated by any of a number of methods. They may be dehydrated in the presence of a hydrophilic agent according to the procedures of Bally et al, copending U.S. application Ser. No. 07/284,751, filed Dec. 12, 1988, entitled "Encapsulation of Antineoplastic Agents in Liposomes", Janoff et al., U.S. Pat. No. 4,880,635, issued Nov. 14, 1989, entitled "Dehydrated Liposomes", Schneider et al., in U.S. Pat. No. 4,229,360, issued Oct. 29, 1980 and Mayer, et al. copending U.S. application Ser. No. 07/636,015, filed Jan. 4, 1991, relevant portions of which are incorporated by reference herein. Alternatively or additionally, the hydrated liposome preparation may also be dehydrated by placing it in surrounding medium in liquid nitrogen and freezing it prior to the dehydration step.

Dehydration with prior freezing may be performed in the presence of one or more protective agents, such as sugars in the preparation according to the techniques of Bally, et al., U.S. Pat. No. 4,880,635, issued Nov. 14, 1989, relevant portions of which are also incorporated by reference herein. Such techniques enhance the long-term storage and stability of the preparations. For example, the agent may be mixed with a sugar solution in a sugar: lipid weight/weight ratio ranging from about 0.5:1 to about 100:1, preferably about 20:1, without affecting the ability of the liposome to retain loaded agent during rehydration. Other suitable methods may be used in the dehydration of the above-disclosed liposome preparations. The liposomes may also be dehydrated without prior freezing.

Once the liposomes have been dehydrated, they can be stored for extended periods of time until they are to be used. The appropriate temperature for storage will depend on the lipid formulation of the liposomes and the temperature sensitivity of encapsulated materials. For example, amino acids and peptides are heat labile, and thus dehydrated liposomes containing such agents should preferably be stored under refrigerated conditions e.g. at about 4° C., so that the potency of the agent is not lost. Also, for such agents, the dehydration process is preferably carried out at reduced temperatures, rather than at room temperature. When the dehydrated liposomes are to be used, rehydration is accomplished by simply adding an aqueous solution, e.g., distilled water or an appropriate buffer, to the liposomes and allowing them to rehydrate. The liposomes can be resuspended into the aqueous solution by gentle swirling of the solution. The rehydration can be performed at room temperature or at other temperatures appropriate to the composition of the liposomes and their internal contents.

The concentration gradient used to generate the transmembrane pH gradient can be created either before dehydration or after rehydration using the external medium exchange techniques described above. For example, the liposomes may be dehydrated prior to establishing the transmembrane pH gradient, for example, dehydrated from their first external medium. Upon rehydration, the pH gradient can be established by admixing the liposomes with the second external medium of relatively acidic or basic pH. The agent can be admixed with the liposomes simultaneously with or following the establishment of the pH gradient. In the case where the liposomes are dehydrated after having a transmembrane pH gradient, the liposomes may be rehydrated by admixing them with an aqueous solution of neutral pH. For example, in the above-mentioned case where liposomes containing citric acid buffer as the first medium are used, the rehydration step would proceed by adding the NaCl/HEPES buffer, and the agent, for example, lysine methyl ester.

Where the liposomes already contain the relatively basic solution (for example, NaCl/HEPES), and therefore already have the transmembrane pH gradient are rehydrated, water or another neutral aqueous solution, and the agent are added. Finally, in the case where liposomes having a transmembrane pH gradient and containing the agent have been dehydrated, rehydration proceeds using water or another aqueous solution. Alternatively, a second agent may be added, if desired.

Liposomes containing the amino acid and peptide formulations of the present invention may be used therapeutically in mammals, especially humans, in the treatment of a number of disease states or pharmacological conditions which require sustained release formulations as well as repeated administration. The mode of administration of the liposomes containing the agents of the present invention may determine the sites and cells in the organism to which the compound may be delivered.

The liposomes of the present invention may be administered alone but will generally be administered in admixture with a pharmaceutical carrier selected with regard to the intended route of administration and standard pharmaceutical practice. The preparations may be injected parenterally, for example, intravenously. For parenteral administration, they can be used, for example, in the form of a sterile aqueous solution which may contain other solutes, for example, enough salts or glucose to make the solution isotonic, should isotonicity be necessary or desired. The liposomes of the present invention may also be employed subcutaneously or intramuscularly. Other uses, depending upon the particular properties of the preparation, may be envisioned by those skilled in the art.

For the oral mode of administration, the liposomal formulations of the present invention can be used in the form of tablets, capsules, lozenges, troches, powders, syrups, elixirs, aqueous solutions and suspensions, and the like. In the case of tablets, carriers which can be used include lactose, sodium citrate and salts of phosphoric acid. Various disintegrants such as starch, lubricating agents, and talc are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added.

For the topical mode of administration, the liposomal formulations of the present invention may be incorporated into dosage forms such as gels, oils, emulsions, and the like. These formulations may be administered by direct application as a cream, paste, ointment, gel, lotion or the like. For administration to humans in the treatment of disease states or pharmacological conditions, the prescribing physician will ultimately determine the appropriate dosage of the agent for a given human subject, and this can be expected to vary according to the age, weight and response of the individual as well as the pharmacokinetics of the agent used.

Also the nature and severity of the patient's disease state or condition will influence the dosage regimen. While it is expected that, in general, the dosage of the drug in liposomal form will be about that employed for the free drug, in some cases, it may be necessary to administer dosages outside these limits.

The following examples are given for purposes of illustration only and are not to be viewed as a limitation of the scope of the invention.

Examples

Materials and Methods

Egg phosphatidylcholine (EPC) was obtained from Avanti Polar Lipids (Birmingham, Ala.). $^{14}$C-methylamine and $^3$H-triphenylphosphonium bromide were purchased from New England Nuclear. All other chemicals used were purchased from Sigma Chemical Co. (St. Louis, Mo.).

Lysine methyl ester was purchased from Sigma Chemical Co. The hydrophobic pentapeptide ($H_3N^+$-Ala-Met-Leu-Trp-Ala-COO; where the carboxyl function was modified to be a methyl ester or amide) was synthesized using the solid phase synthesis method of de Kroon et al., 1989, BBA, 981:371.

EXAMPLE 1

Loading of Lysine Methyl Ester by liposomal transmembrane pH Gradients - EPC vesicles Multilamellar vesicles (MLVs) were produced by hydrating 50 mg EPC in 1.0 ml citrate (300 mM) buffer at pH 4.0. The MLVs were frozen in liquid nitrogen and thawed in water at about 50°–60° C. for five freeze-thaw cycles.

The resulting MLVs were extruded ten times through two stacked 100 nm pore size polycarbonate filters (Nuclepore) employing a device obtained from Lipex Biomembranes Inc. (Vancouver, Canada) as set forth in Hope et al., 1985, BBA, 812:55. The resulting large unilamellar vesicles (LUVs) were 108 nm in diameter as determined by quasielastic light scattering (QELS) employing a NICOMP particle sizer.

The LUVs in the pH 4.0 media were passed down a 10 cm Sephadex G-50 (medium) column previously equilibrated with 150 mM NaCl, 20 mM HEPES (pH 7.5) (Hepes buffered saline or "HBS"), to generate the pH 7.5/4.0 exterior/interior pH gradient.

Uptake of the lysine methyl ester was initiated by first dissolving 0.47 mg of the lysine methyl ester in 1.0 ml of HBS medium 2.0 mM lysine methyl ester) to which 0.25 ml of the LUVs exhibiting the pH gradient were added. The liposomes were incubated at 23° C. and aliquots of 0.1 ml were removed at selected times (see FIG. 1) from this incubation mixture, and untrapped material removed by passage through 1 ml (dry) Sephadex G-50 column, centrifuged for 1 minute at 2500 rpm.

EXAMPLE 2

Control for no pH gradient

The methods of Example 1 were repeated wherein the LUVs in the pH 4.0 media were passed down a 10 cm Sephadex G-50 (medium) column previously equilibrated with 300 mM citrate buffer, at pH 4.0, thus generating no pH gradient.

Similarly the methods were repeated wherein the LUVs were made in pH 7.5 media and passed down a 10 cm Sephadex G-50 (medium) column previously equilibrated with 150 mM NaCl, 20 mM HEPES, at pH 7.5 (Hepes buffered saline or "HBS"), thus generating no pH gradient.

EXAMPLE 3

Determination of loaded lysine methyl ester in EPC LUVs

Lysine methyl ester concentrations inside the LUVs of Examples 1 and 2 were determined by a modification of the technique employed by Hope and Cullis, 1987, J. Biol. Chem., 262:4360, employing TNBS (trinitrobenzenesulfonic acid) to label primary amino groups of lysine methyl ester. The buffer used for the labelling was 100 mM $NaHCO_3$, 50 mM $H_3BO_3$, at pH 10.0. A reference cuvette containing 2.5 ml of buffer (pH 10.0) was placed in the reference beam. The sample cuvette contained 2.5 ml of buffer (pH 10.0) with 0.5 mM TNBS aliquots (50 ul) of vesicles containing lysine methyl ester were then added. The resulting change in absorbance was measured at 420 nm after incubation in the dark for 1 hour. Triton X-100 (200 ul, 0.5%) was added to both cuvettes to solubilize the vesicles and thus expose all primary amino groups present to the TNBS. The absorbance in the presence of detergent was taken to represent 100% labelling.

EXAMPLE 4

Measurement of pH gradients and membrane potentials

The magnitude of the pH gradients and membrane potentials present were measured using $^{14}$C-methylamine and $^3$H-triphenylphosphonium bromide ($^3$H-TPP) respectively as indicated in Hope et al., 1985, BBA, 812:55 and in Madden et al., 1990, Chem. Phys. Lipids, 53:37. The concentrations used were 1 uCi/ml. The amount of probe accumulated was determined via liquid scintillation counting. Transmembrane pH gradients could then be calculated using the relationship pH=log ([Methylamine]$_{in}$/[Methylamine]$_{out}$) as indicated in Mayer et al., 1988, Biochemistry, 27:2053. Membrane potentials were calculated similarly for $^3$H-TPP (see Hope et al., 1985, BBA, 812:55).

EXAMPLE 5

Measurement of phospholipid concentrations

Phospholipid concentrations were calculated by a modification of the method of Fiske and Subbarow, 1925, J. Biol. Chem., 66:375. Typical phospholipid concentrations were approximately 3.0 mM.

EXAMPLE 6

Results of loading of lysine methyl ester into EPC LUVs

FIG. 1 demonstrates that lysine methyl ester is rapidly accumulated into EPC LUVs by the methods of Example 1 with an acidic interior (wherein $pH_i=4.0$ and $pH_o=7.5$). The amino acid loaded quickly with maximal levels being loaded with the first 5–10 minutes of incubation. A corresponding decrease in the measured pH gradient was also observed wherein the gradient dropped from 3.5 to 1 pH unit; such drop in the residual pH gradient being due to protonation of the methyl ester after traversal of the membrane in the neutral form. The maximal concentrations entrapped were about 85 nmoles lysine methyl ester/umole phospholipid. This high level of uptake was maintained for at least 24 hours with no leakage of the lysine methyl ester.

In the case wherein the liposomes exhibited no pH gradient (see Example 2 above), but wherein both the interior and exterior bathing solutions were pH 4.0 (4.0/4.0) or wherein both were pH 7.5 (7.5/7.5), little lysine methyl ester was taken up into the LUVs (only about 10% of that observed for the vesicles with a pH gradient).

EXAMPLE 7

Loading of Lysine Methyl Ester by liposomal transmembrane pH Gradient - EPC:cholesterol vesicles EPC:cholesterol vesicles (55:45 mole %) were made by dissolving 43 mg EPC and 17 mg cholesterol in 1.0 ml of chloroform. The chloroform was then removed under a stream of nitrogen and by subsequent storage under reduced pressure. The methods of Example 1 were employed using 20 ml of citrate buffer (pH 4.0) to produce frozen-and-thawed MLVs which were then likewise extruded to form LUVs. In the case of EPC:cholesterol vesicles, the extrusion step took place at 65° C.

A pH gradient was established and the lysine methyl ester was loaded into the vesicles as disclosed in Example 1, at 20° C.

The above method was repeated with the loading step of the lysine methyl ester carried out at 4° C. and 37° C. The methods of Examples 3, 4, and 5 were followed to determine the extent of loading of the lysine methyl ester in the EPC:cholesterol vesicles.

Figure 2:
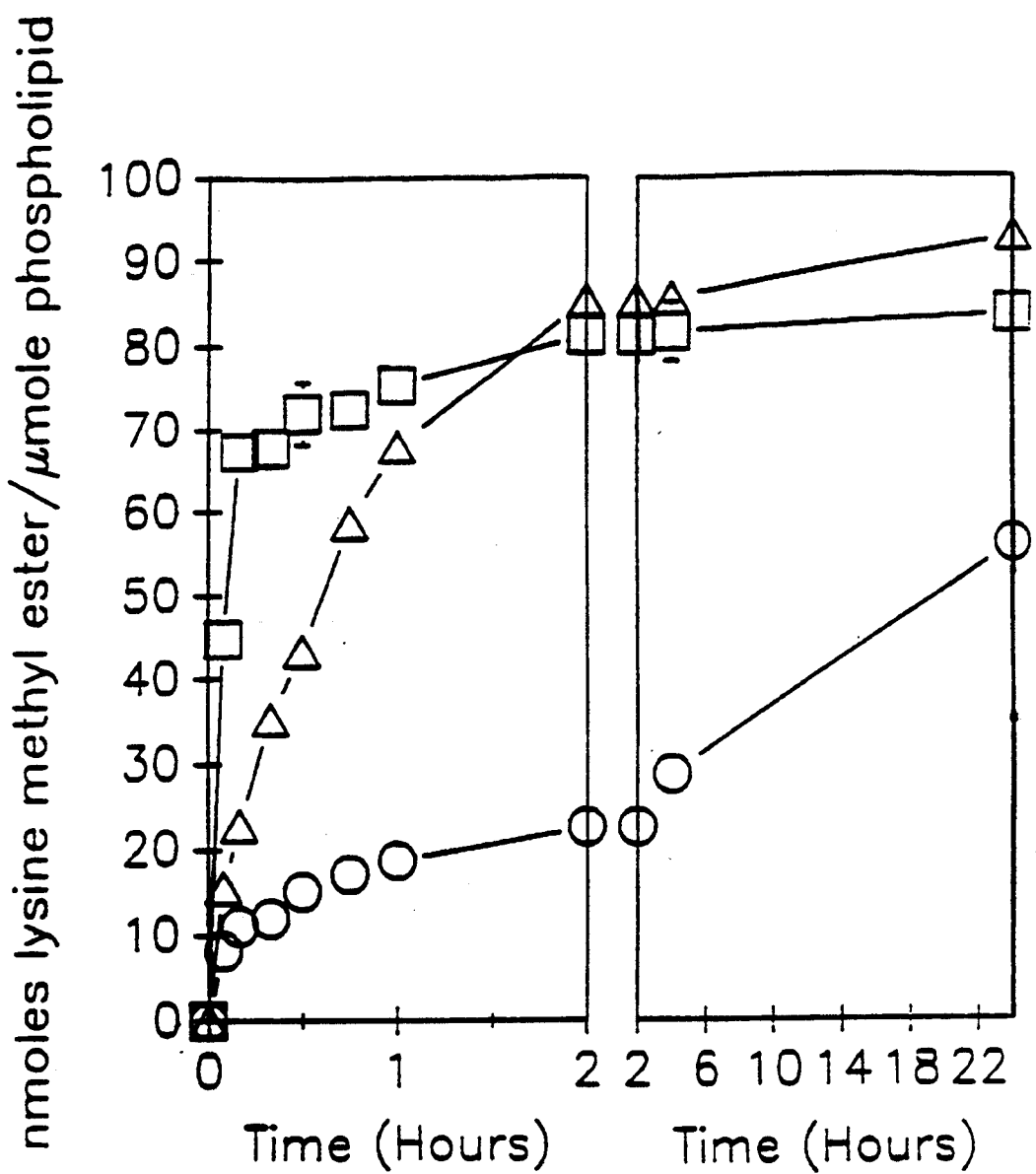
FIG. 2 graphically represents the time course of uptake of lysine methyl ester into 100 nm EPC:cholesterol vesicles (55:45 mole %) bearing a 7.5/4.0 (external/internal) pH gradient. Uptake was conducted at 4° C. (open circles), 20° C. (open triangles), and 37° C. (open squares). The external concentration of lysine methyl ester was 2.0 mM.
Figure 3:
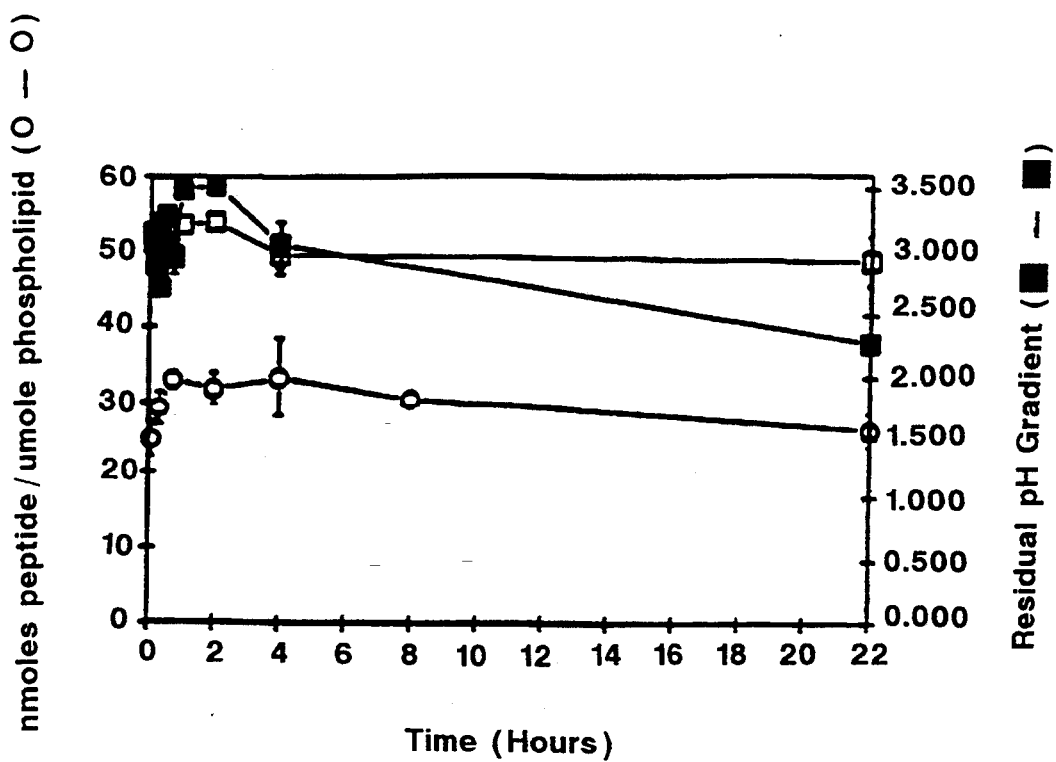
FIG. 3 graphically represents the time course of uptake of Lys-Tyr-Trp-Trp-Phe-Amide into 100 nm EPC vesicles bearing a 7.5/4.0 (external/internal) (open squares) and a 7.5/7.5 (external/internal) (open circles) pH gradient. Uptake was conducted at 23° C. The external concentration of Lys-Tyr-Trp-Trp -Phe-Amide was 76 uM.

FIG. 2 is a graphic representation of the time course of the amino acid loading into LUVs exhibiting the pH gradient of 7.5/4.0 (external/internal). The time course of uptake is reported at uptake incubation temperatures of 37° C., 20° C., and 4° C. Very high levels of loading (approximately 70 nmoles/umole phospholipid) were achieved within 10 minutes at 37° C., 1 hour at 20° C., and potentially after more than 22 hours at 4° C. The amount of lysine methyl ester entrapped was again found to remain quite stable, even after long time periods (more than 20 hours) at elevated temperatures (37° C.).

EXAMPLE 8

The methods of Example 1 were employed wherein the amino acid Lysine ethyl ester was loaded into LUVs following incubation at 23° C. for 1 hour. Loading of this amino acid derivative occurred at a value of 378.0 nmoles peptide/umole phospholipid.

EXAMPLE 9

The methods of Example 1 were employed wherein the peptide Bombesin (pGlu-Gln-Arg-Leu-Gly-Asn-Gln-Trp-Ala-Val-Gly-His-Leu-Met-$NH_2$) was loaded into LUVs following incubation at 23° C. for 1 hour. Loading of this peptide derivative occurred to a value of 34.6 nmoles peptide/umole phospholipid.

EXAMPLE 10

The methods of Example 1 were employed wherein Gastrin-Related Peptide (N-t-BOC-Trp-Met-Asp-Phe-$NH_2$) was incubated with the LUVs at 23° C. for 1 hour. Following this incubation time period, 25.1 nmoles peptide/umole phospholipid was loaded into the LUVs.

EXAMPLE 11

The methods of Example 1 were employed wherein 74 ug of the peptide Growth Hormone Releasing Factor Fragment (Lys-Tyr-Trp-Trp-Phe-$NH_2$) was incubated with the LUVs at 60° C. for 2 hours. Following this incubation time period, 195.0 nmoles peptide/umole phospholipid was loaded into the LUVs.

EXAMPLE 12

The methods of Example 1 were employed wherein 74 ug of the peptide Growth Hormone Releasing Factor Fragment (Lys-Tyr-Trp-Trp-Phe-$NH_2$) was incubated with the LUVs at 23° C. for 2 hours. Following this incubation time period, about 55 nmoles peptide/umole phospholipid was loaded into the LUVs.

COMPARATIVE EXAMPLE 13

The methods of Example 1 were employed wherein 0.48 mg of the amino acid derivative histidine methyl ester (Sigma Chemical Co., St. Louis, Mo.) was incubated at 23° C. with the LUVs. After an incubation of 1 hour, no loading took place (0 nmoles peptide/umole lipid loaded).

COMPARATIVE EXAMPLE 14

The methods of Example 1 were employed wherein 0.34 mg of the peptide $(Lys)_5$methyl ester was incubated at 23° C. with the LUVs. Following an incubation of about 1 hour, no loading took place (0 nmoles peptide/umoles lipid loaded).

COMPARATIVE EXAMPLE 15

The methods of Example 1 were employed wherein 0.95 mg of the peptide (Lys-$(Ala)_4$) methyl ester was incubated at 23° C. with the LUVs. Following an incubation of about 1 hour, no loading took place (0 nmoles peptide/umoles lipid loaded).

We claim:

1. A liposome which comprises a lipid and a peptide, wherein a terminal carboxyl group of the peptide is modified to a non-acidic functional group such that the peptide has weak acid or base characteristics.

2. The liposome of claim 1, wherein the lipid is egg phosphatidylcholine and the liposome further comprises cholesterol in a 45:55 (mole:mole) ratio with the egg phosphatidylcholine.

3. The liposome of claim 1, wherein the lipid comprises diarachidonoyl phosphatidylcholine, dimyristoyl phosphatidylcholine, dipalmitoyl phosphatidylcholine and distearoyl phosphatidylcholine.

4. The liposome of claim 1, wherein the peptide is selected from the group consisting of a bombesin peptide having the sequence pGlu-Gln-Arg-Leu-Gly-Asn-Gln-Trp-Ala-Val-Gly-His-Leu-Met-amide, a gastrin-related peptide having the sequence N-t-BOC-Trp-Met-Asp-Phe-amide, a growth hormone-releasing peptide having the sequence Tyr-Gly-Trp-Phe-Phe-amide and a growth hormone-releasing factor fragment having the sequence Lys-Tyr-Trp-Trp-Phe-amide.

5. The liposome of claim 1, wherein the non-acidic functional group is an ester or an amide group.

6. The liposome of claim 1, wherein the liposome is dehydrated.

7. A pharmaceutical composition comprising the liposome of claim 1 and a pharmaceutically acceptable carrier.

8. The liposome of claim 1, wherein the liposome is a large unilamellar vesicle.

9. The liposome of claim 8, wherein the diameter of the large unilamellar vesicle is from about 60 nm to about 300 nm.

10. The liposome of claim 1, further comprising an ionic gradient across the outer bilayer of the liposome.

11. The liposome of claim 10, wherein the ionic gradient is a $Na^+$, $K^+$, $Cl^-$, $Li^+$ or a pH gradient.

12. The liposome of claim 11, wherein the ionic gradient is a pH gradient.

13. The liposome of claim 12, wherein the pH gradient comprises an acidic solution internal to the liposome and an external solution which is basic relative to the internal acidic solution.

14. The liposome of claim 13, wherein the external basic solution is a sodium carbonate, sodium biphosphate or sodium chloride/HEPES buffer.

15. The liposome of claim 13, wherein the internal acidic solution has a pH of about 4.0.

16. The liposome of claim 15, wherein the internal acidic solution is a citric acid buffer.

* * * * *